United States Patent [19]

Arhan et al.

[11] Patent Number: 4,566,465

[45] Date of Patent: Jan. 28, 1986

[54] PROBE WITH VARIABLE GEOMETRY FOR MEASURING THE RADIAL STRAINS IN A SPHINCTER OF A LIVING ORGANISM

[75] Inventors: Pierre J. Arhan, Paris; Marc R. Héro, Pontoise, both of France

[73] Assignee: Universite Rene Descartes Paris V, Paris, France

[21] Appl. No.: 597,535

[22] Filed: Apr. 6, 1984

[30] Foreign Application Priority Data

Apr. 7, 1983 [FR] France .................. 83 05678

[51] Int. Cl.$^4$ .............................................. A61B 19/00
[52] U.S. Cl. .................................... 128/778; 128/341; 128/774
[58] Field of Search ............... 128/778, 780, 774, 668, 128/672, 673, 675, 692, 748, 782, 341, 343; 33/174 D, 1 SP, 302, 303; 72/117, 115; 73/1 B, 151, 623

[56] References Cited

U.S. PATENT DOCUMENTS

| | | | |
|---|---|---|---|
| 1,271,456 | 7/1918 | Flack | 128/341 |
| 1,737,488 | 11/1929 | Zohlen | 128/341 |
| 3,164,009 | 1/1965 | Schaschl et al. | 73/151 |
| 4,306,459 | 12/1981 | Johnson et al. | 73/623 |

FOREIGN PATENT DOCUMENTS

| | | | |
|---|---|---|---|
| 6944852 | 8/1971 | France | 128/341 |
| 181778 | 10/1966 | U.S.S.R. | 128/782 |
| 733650 | 5/1980 | U.S.S.R. | 128/774 |
| 843954 | 7/1981 | U.S.S.R. | 128/774 |

OTHER PUBLICATIONS

"Miniature Piezoresistive Transducers for Transient Soft-Body Contact-Stress Problems" by T. Brown et al.; Experimental Mechanics, Jun. 1979, pp. 214–219.

*Primary Examiner*—William E. Kamm
*Assistant Examiner*—David Shay
*Attorney, Agent, or Firm*—Lerner, David, Littenberg, Krumholz & Mentlik

[57] ABSTRACT

A probe for studying the visco-elastic behavior of sphincters of living organisms is comprised of an expansible head formed by three articulated groups disposed radially at 120° intervals about a central axis. Each of the articulated groups is composed of a cross-piece which interconnects a rigid member, carrying a strain gauge on its outer surface, to the central axis. The cross-pieces are articulated at one end about the opposite ends of the rigid member and are articulated at the other end about two blocks which are carried by the central axis. The cross-pieces are constructed such that rotation of the central axis causes the distance between the rigid elements and the central axis to vary. A flexible shaft couples the central axis to a motor.

10 Claims, 7 Drawing Figures

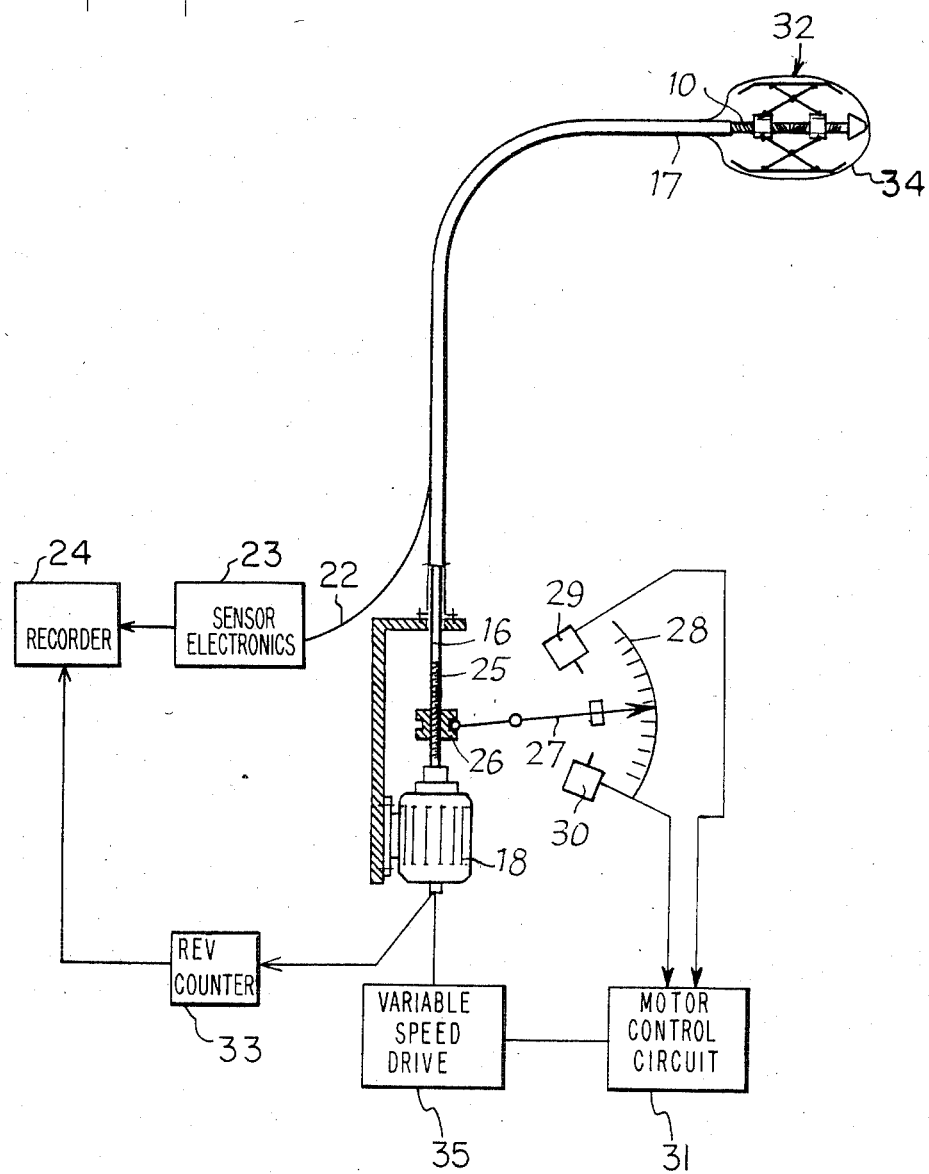

PROBE WITH VARIABLE GEOMETRY FOR MEASURING THE RADIAL STRAINS IN A SPHINCTER OF A LIVING ORGANISM

The present invention relates to a probe with variable geometry for measuring the radial strains in a sphincter of a living organism, comprising a radially expansible head provided with members for measuring the strains on its periphery.

A study of the mechanical properties of gastro-intestinal sphincters and the variations thereof in time is known to have been undertaken. It appears at present that the radial strains exerted by the sphincters depend on the diameter of the probes which are introduced therein. Now, the probes incorporating inflatable bags which are usually employed do not lend themselves well to measuring the diameter that they impose on the sphincters nor to that of the strain which the latter exert, when the pressure created in the inflatable bags increases to such a point that they are the seat of hernias upstream or downstream of the sphincter. Moreover, measurements must be renewed with probes of different diameter, being given that the radial strain imposed by the sphincter depends on the diameter of the probe.

It is an object of the invention to create a probe of the type in question, which allows precise measurements of diameter and of pressure in the course of cycles executed at determined speeds of expansion and retraction, and which may thus be used for establishing both the viscous and elastic properties of the sphincters.

To this end, according to the invention, the expansible head of the probe is constituted by an expansible assembly of articulated, rigid elements which are constantly located within a surface of revolution of variable radius, preferably cylindrical, and whose expansion and retraction are controlled by a motor to which it is mechanically connected by a flexible connecting means, whilst the measuring members are pressure sensors, such as strain gauges or piezo-electric sensors or sensors with electromagnetic induction, disposed on the periphery of said assembly. The radius of such a probe is always perfectly defined and may be known with precision at any moment, for example by means of an electronic rev counter coupled to the motor. Similarly, the sensors permanently furnish an exact measurement of the strains generated by the sphincter.

In a preferred embodiment, the above-mentioned assembly of articulated rigid elements comprises a plurality of cross-pieces, for example three in number, regularly distributed in star-form about a central axis. The arms of each cross-piece are articulated at their outer ends about the ends of an oblong sole guided so as to remain parallel to said axis and provided on its outer face with a pressure sensor, and at their inner ends about a pair of block elements adapted to be moved towards or away from each other along said axis under the action of said motor. The soles may be guided in a simple manner by providing that one of the arms of each cross-piece bears a finger which slides in a slot made in the other arm along a line such that the corresponding sole is forced to remain parallel to the axis of the head of the probe. Said block elements preferably comprise inner threads of opposite direction and are mounted respectively on one and the other of the parts of a threaded rod with double reverse pitch; this rod, disposed along said axis, is connected to the motor by a flexible shaft for driving in rotation. Furthermore, the pressure sensors are preferably connected to the inner face of elastic blades of which each is fixed by one end to the outer face of the corresponding sole to extend substantially parallel to said face.

In order to maintain the expansible head in the sphincter where it is placed, the peripheral soles of which it is comprised may be provided with ends dished towards the outside which fit on each side of the sphincter. However, it is preferable if the soles simply have a length greater than the axial extent of the sphincter for which the probe is intended.

A rev counter is suitably coupled with said means for mechanical connection to the motor, which rev counter enables the diameter of the expansible head to be known at any moment. The rev counter preferably belongs to an electronic module which delivers a signal expressing the deformation imposed on the sphincter as a function of the number of revolutions of the motor. Moreover, this mechanical connecting means is advantageously coupled with end-of-stroke devices which control automatic reversal of the direction of rotation of the motor when the expansible head attains either its minimum or its maximum diameter, in order to avoid any excessive effort both on the sphincter under examination and on the probe.

To allow the speed of expansion and contraction of the expansible head to be selected, the motor is suitably provided with a variable speed drive. Furthermore, by reason of the risk of corrosion due to the presence of sometimes aggressive juices in living organisms, said head is advantageously enclosed in a tight protective envelope 34 which is sufficiently supple not to flasify the measurements of pressure.

The invention will be more readily understood on reading the following description with reference to the accompanying drawings, in which.

FIG. 5 schematically shows the assembly constituted by the probe and its accessories.

Figure 6:
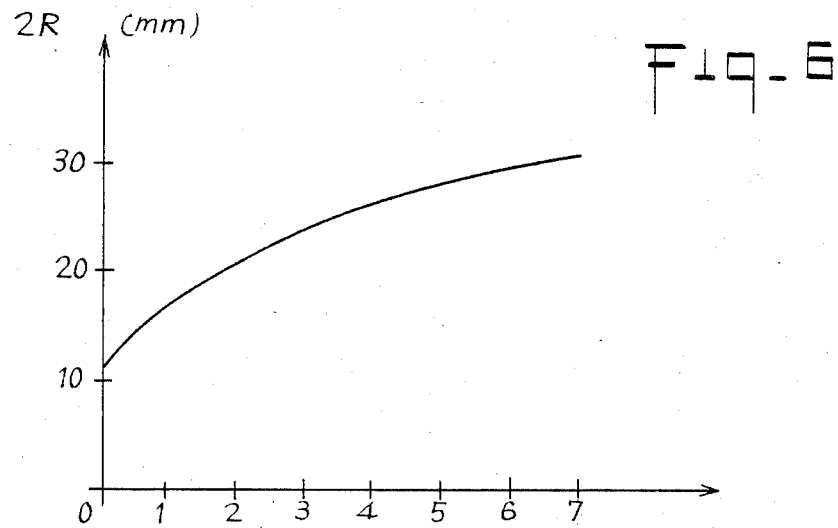

FIG. 6 shows a graph representing the relation between the diameter of the probe and the number of revolutions of its drive motor.

Figure 7:
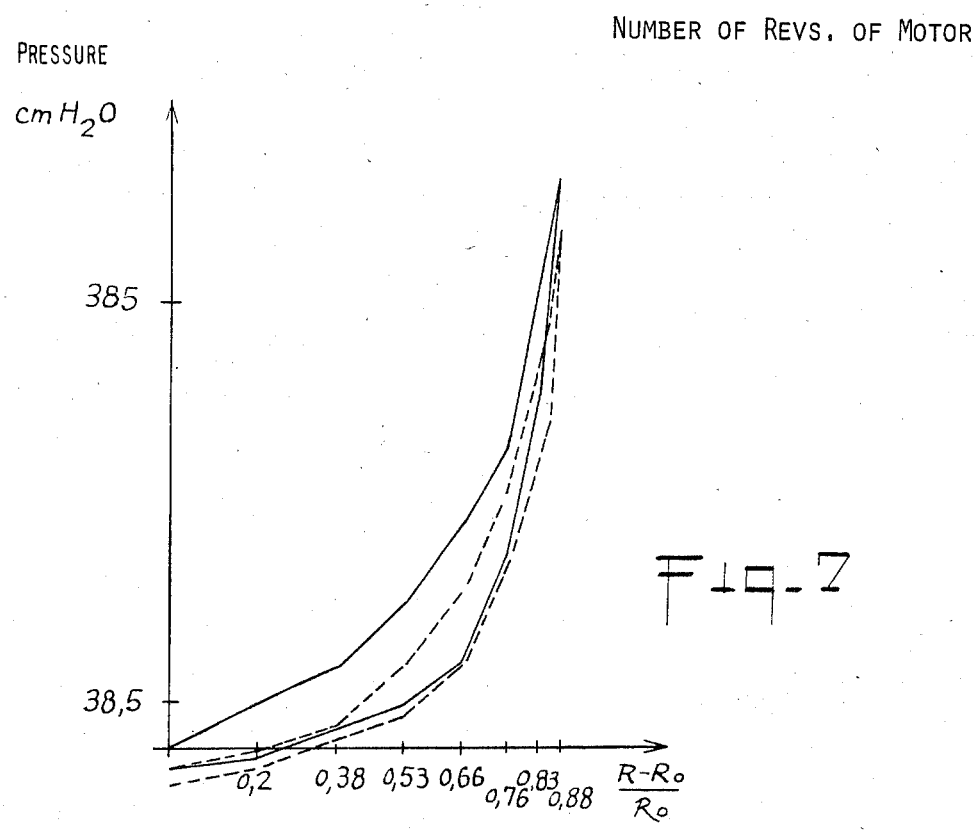

FIG. 7 shows pressure curves of a sphincter as a function of the rate of expansion of the probe.

Figure 1:
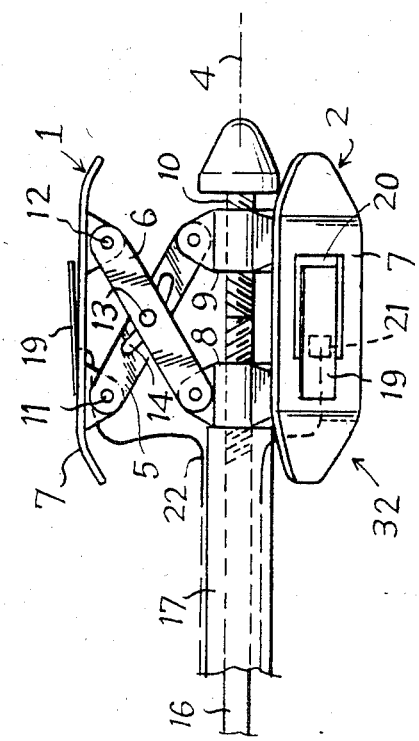
FIG. 1 shows a probe according to the invention in side elevation.
Figure 2:
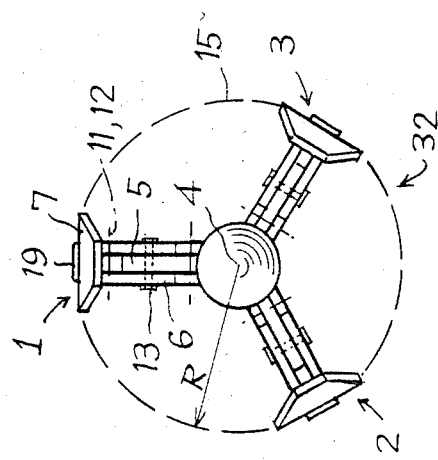
FIG. 2 shows a front view of the probe of FIG. 1.
Figure 3:
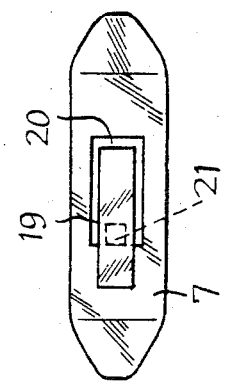
FIG. 3 shows in plan one of the soles of the probe of FIGS. 1 and 2.

Referring now to the drawings, the probe shown in FIGS. 1 and 2 is constituted by an expansible head 32 comprising three identical deformable articulated groups 1, 2, 3, disposed radially at 120° with respect to one another about an axis 4. Each group 1, 2 or 3 comprises a cross-piece formed by two arms 5, 6 of the same length, whose outer ends are articulated on an oblong sole 7 at two spaced apart points thereon, designated by references 11 and 12, and whose inner ends are respectively articulated on two block elements 8, 9 each screwed on one of the parts of a rotating rod 10 with double reverse pitch, disposed along axis 4. In order to ensure that the soles 7 are constantly maintained parallel to axis 4, the arm 6 of each cross-piece comprises, at its intersection with the arm 5, a finger 13 which slides in a slot 14 made in the arm 5 along a curved line designed to that end.

The soles 7, whose outer face is contained in a plane perpendicular to the corresponding radial direction, are thus regularly distributed over a virtual cylindrical surface 15 whose axis merges with axis 4. The rod 10 is connected to a motor 18 (FIG. 5) by a flexible steel cable 16 which is surrounded by a stationary flexible sheath 17 connected at one end to the casing of the motor and at the other end to the block element 8, preventing the latter, and consequently the whole of the expansible head, from rotating. When the rod 10 has been rotated by means of the motor 18, the block elements 8 and 9 move apart from or towards each other, so that the articulated elements 1, 2 and 3 simultaneously undergo an expansion or a retraction with the radius R of the cylindrical surface 15 on which the soles 7 lie, varying accordingly.

On the outer face of each sole 7 there is welded an elastic blade 19 extending in a plane which is very slightly oblique towards the outside with respect to the plane of the sole and opposite a rectangular opening 20 made in said sole. On the inner face of this blade there is mounted a pressure sensor constituted by a strain gauge 21. The three strain gauges 21 are connected, by electrical conductors 22 running along the flexible lead 16, 17 for actuating the head 32 (FIG. 5), to an electronic assembly comprising a supply and amplifier module 23 and a recorder 24.

At its end connected to the motor 18, the cable 16 comprises a threaded rod 25 on which is screwed a non-rotating block element 26. This block element, when the motor 18 rotates, moves along the threaded rod 25, driving an indicator needle 27 along a dial 28 graduated in number of revolutions of the cable 16. The position of the needle 27 on the dial 28 makes it possible to know the diameter 2R of the head 32 with the aid of a graph such as that of FIG. 6; by the very structure of said head, the relation between its diameter and the number of revolutions is in fact not linear. The needle 27 is furthermore adapted to act on end-of-stroke switches 29, 30 which trigger a reversal of the direction of rotation of the motor 18, via the control circuit 31 thereof.

The motor is also connected to an electronic module 33 comprising a rev counter and delivering a signal which expresses the deformation imposed by the probe as a function of the number of revolutions of the motor 18, as well as the speed of development of this deformation. After appropriate processing, this signal is sent to the recorder 24.

Once the strain gauges 21 have been calibrated, by application of known pressures thereon, the probe is introduced into the sphincter whose properties are to be examined (for example the anal sphincter or the cardial sphincter) and the pressure which it exerts on the probe for different diameters 2R given thereto is noted, and this during successive cycles of expansion-retraction of which the duration may be adjusted by means of a variable speed drive 35. The variable speed drive could alternatively be included in the control circuit 31 of the motor 18. The curves of FIG. 7, obtained by means of the recorder 24, are given by way of example of results obtained. These curves, which indicate the pressure of the sphincter as a function of the rate of expansion of the probe (relative value of the radius R of said probe with respect to its minimum radius $R_o$), and this over two successive cycles, show the hysteretic behaviour of the sphincter under examination. The first cycle is shown in solid lines and the second in broken lines. The speed of expansion is constant and corresponds to an expansion time of 15 seconds.

The establishment of such networks of experimental curves makes it possible, by processing the data obtained, to develop mathematical models giving an account of the visco-elastic behaviour of the different sphincters of the human organism.

Figure 4:
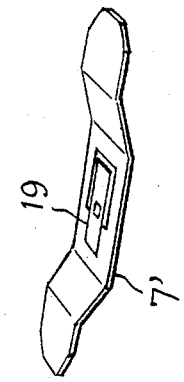
FIG. 4 shows a variant embodiment of a sole, in perspective.

FIG. 4 shows a variant in which soles 7' are used whose ends are raised towards the outside in order to prevent the probe from escaping from the sphincter during examination. However, it generally suffices to use to the same end substantially flat soles 7 presenting a much greater length than that of the sphincter in question, for example two or three times longer.

The control circuit 31 of the motor 18 comprises, in addition to the elements which have been mentioned above, elements which make it possible to manually stop the motor or to reverse the direction of rotation thereof, in order to limit to any desired value the expansion imparted by the probe to the sphincter in which it is placed. In addition, a brake is associated with the motor 18, which operates only for a short time (for example one tenth of a second) in order to stop the motor whenever it changes direction, this in order to lessen the phenomena of self-induction which are produced whenever the direction of the motor is reversed.

What is claimed is:

1. A probe having a variable width for measuring the radial strain of a sphincter of a living organism, comprising:
    a rotatable threaded rod;
    at least three pressure sensors;
    at least three flat rigid elements each carrying one of said pressure sensors for engaging and for measuring the radial strain of said sphincter of a living organism;
    a pair of threaded block elements carried by said threaded rod, said block elements including inner threads such that the blocks move in opposite directions along said threaded rod during rotation thereof;
    means for connecting said rigid elements to said block elements such that rotation of said threaded rod causes the distance between said threaded rod and said rigid elements to vary;
    motor means for rotating said threaded rod at a constant rate; and
    means responsive to said pressure sensors for indicating the radial strain of said sphincter of a living organism.

2. The probe of claim 1 wherein said means for connecting includes at least three pairs of crossed-members regularly distributed about said threaded rod, each of said pairs including two inner ends articulated about said pair of block elements and two outer ends articulated about the opposite ends of one of said rigid elements, each pair of crossed-members including one member having a slot therein and one member having a finger which engages said slot, said slot having a configuration such that said rigid elements remain parallel to said threaded rod during rotation thereof.

3. The probe of claim 1, wherein said threaded rod includes a threaded rod having a double reverse pitch and wherein said block elements include inner threads of opposite direction.

4. The probe of claim 1 additionally comprising at least three elastic blades, with each rigid element supporting one of said elastic blades, said blades being fixed at one end to said rigid elements and extending substantially parallel thereto, said pressure sensors being carried on the inner surfaces of said elastic blades.

5. The probe of claim 1 wherein the rigid elements have a length somewhat greater than the axial extent of the sphincter for which it is intended.

6. The probe of claim 1 wherein said means for rotating said threaded rod includes an electric motor and flexible coupling means coupling said motor to said threaded rod.

7. The probe of claim 6 additionally comprising means responsive to the number of revolutions of said motor for producing a signal representative of the distance between said threaded rod and said rigid elements.

8. The probe of claim 6 additionally comprising means for automatically reversing the direction of rotation of said motor when said rigid elements reach one of a maximum and minimum distance from said threaded rod.

9. The probe of claim 6 additionally comprising a variable speed drive for controlling the speed of said motor.

10. The probe of claim 1 additionally comprising a flexible protective envelope encompassing said rigid elements.

* * * * *